United States Patent [19]

King

[11] Patent Number: Plant 5,554

[45] Date of Patent: Sep. 10, 1985

[54] ELM TREE

[76] Inventor: Benjamin J. King, 4600 Millers Station Rd., Hampstead, Md. 21074

[21] Appl. No.: 635,155

[22] Filed: Jul. 27, 1984

[51] Int. Cl.[3] ..... A01H 5/12

[52] U.S. Cl. ..... Plt./51

[58] Field of Search ..... Plt./51

*Primary Examiner*—Robert E. Bagwill

*Attorney, Agent, or Firm*—Webb, Burden, Robinson & Webb

[57] ABSTRACT

A new variety of *Ulmus parvifolia* is characterized by its rapid growth rate, propagation rate and its leaf appearance which is dark, leathery and semi-glossy in comparison to other varieties.

4 Drawing Figures

BACKGROUND OF THE NEW TREE

The present invention comprises a new and distinct variety of *Ulmus parvifolia* (Chinese elm) known by the varietal name King's Choice.

The Chinese elm is an excellent tree for landscaping and is resistant to the Dutch elm disease. The Chinese elm is often confused with the Siberian elm (*Ulmus pumula*) which has several inferior characteristics. The Chinese elm flowers and fruits in the fall whereas the Siberian elm flowers and fruits in the spring and is a more dirty tree. The Siberian elm has more brittle limbs, doesn't self-repair and is more prone to attack by insects as compared with the Chinese elm.

The new variety of Chinese elm is characterized by a rapid growth rate and its dendritic pattern through at least the the first seven years. The new variety also roots readily through leaf propagation with and without hormones or other root stimulating materials. The leaves are darker, more luxuriant and possess a pleasant leathery semi-glossy surface appearance as compared to other open pollinated varieties of *Ulmus parvifolia.* The new variety has been found to retain its distinctive characteristics through successive propagations.

The new variety was disclosed at King's Men Tree Farms, Hampstead, Md., in 1979 among a group of 1000 random open pollinated seedlings of *Ulmus parvifolia* which had been acquired from Cully Nursery, Springfield, Ill., as one year liners. These seedlings had been germinated in the spring of 1977 and planted by King's Men Tree Farms in April of 1978. In 1979 and continuing in 1980, the specimen tree was found to be growing at more than twice the rate of the remainder of the trees. In the spring of 1981, the specimen tree was tagged, has never been transplanted, and has been carefully monitored ever since.

DESCRIPTION OF THE NEW TREE

Figure 1:
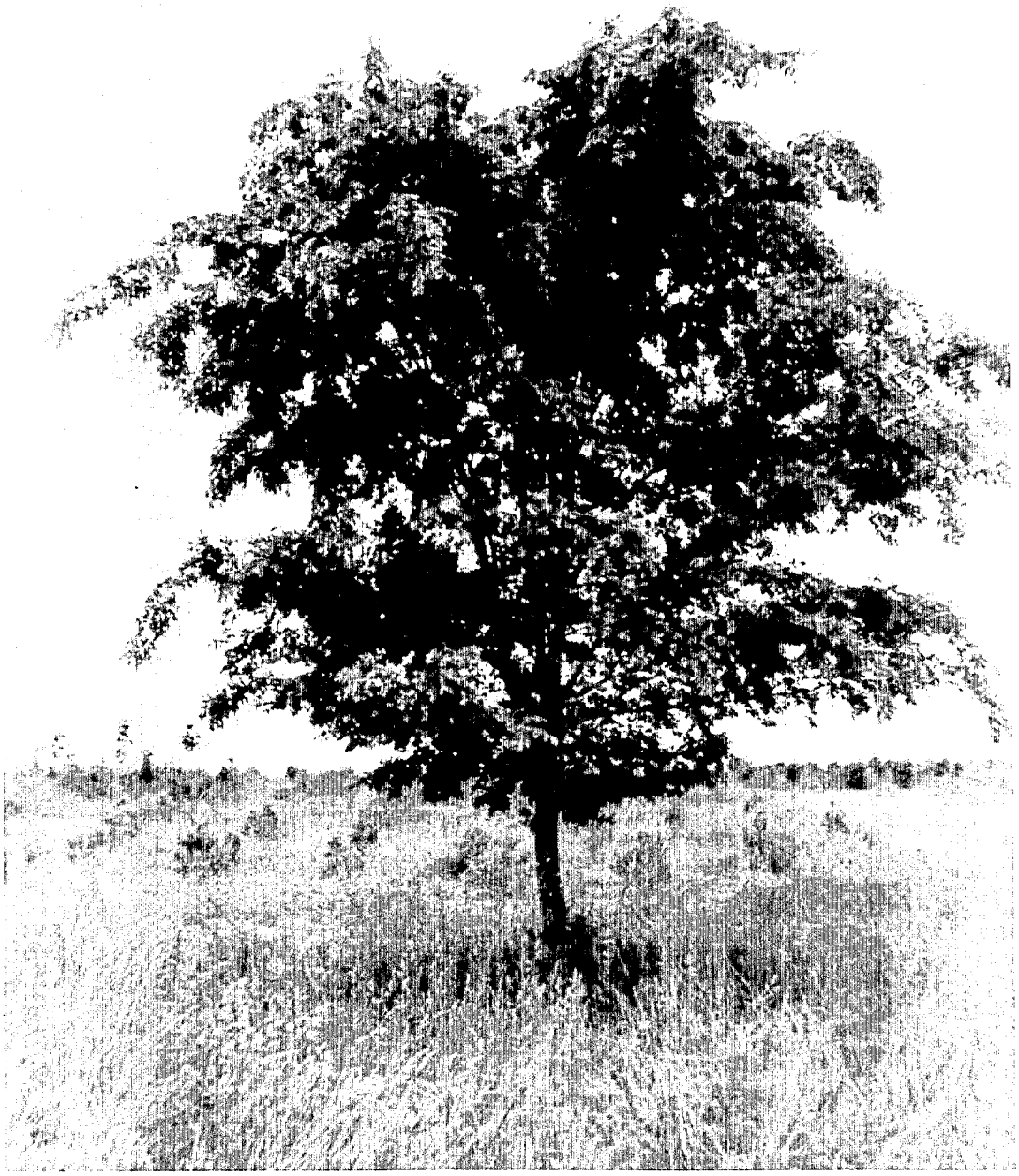
FIG. 1 is a photograph of the new variety at seven years of growth.

The new variety is shown in FIG. 1 after a seven year growth. The tree has a height of 22 feet from the soil line and a width of 16 feet measured at the point of greatest spread, or a height-to-width ratio of 1.4 to 1.0.

The dendritic pattern of the tree in a single bole which divides into laterals at angles greater than 90° above the horizon, which then droop to a canopy silhouette much like the American elm (*Ulmus americana*). This drooping feature does not appear with any of the open pollinated trees growing in the same ambience.

The mature leaf has a generally oblanceolate form. The leaf margin is serrated, having 19–20 serrations along each edge. The mature leaf size is on the order of 6.5×3.1 cm. The mature leaf color in Maryland, one month from leaf bud break, was R.H.S. Green Group 137D. In the fall, the leaves turn to a dull yellow color before they fall. The leaves possess a leathery, semi-glossy surface appearance which distinguishes the new variety from all other known elms.

Figure 2:
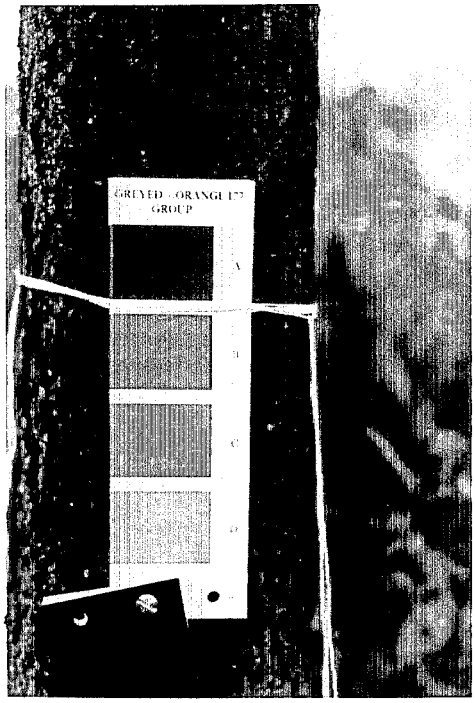
FIG. 2 is a photograph of the trunk having an R.H.S. color panel attached.
Figure 3:
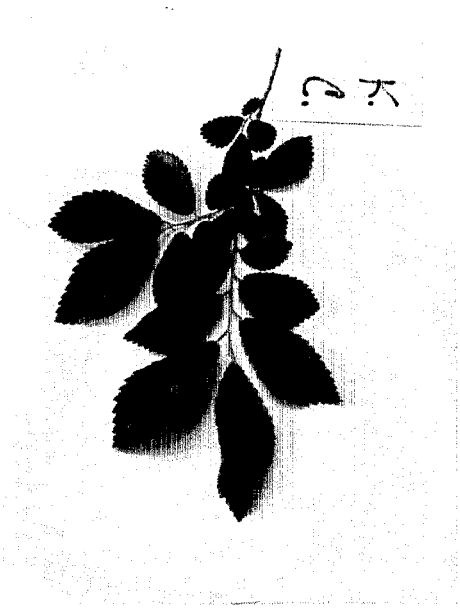
FIG. 3 is a photograph of a branch showing the leathery surface of the leaves.
Figure 4:
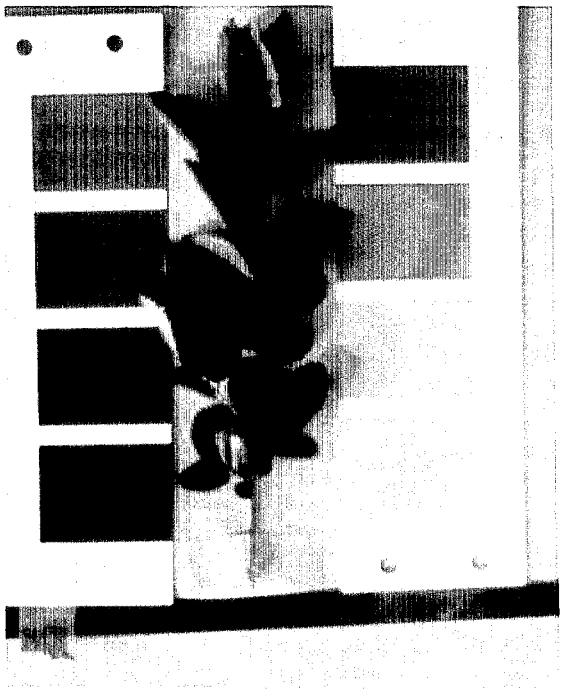
FIG. 4 is a photograph of a branch including mature leaves alongside an R.H.S. color panel.

The bark of the tree, as shown in FIG. 2, can be distinguished from the bark of the open pollinated *Ulmus parvifolia.* The subject bark is more uniform in color and has regular channels as compared with the remainder of the open pollinated trees which tend to be more blotchy in appearance and are generally referred to as "lace bark" because of the natural mottling. The mature bark, at a distance, has a color of R.H.S. Greyed-Orange Group 177A and the bark underlaid in exposed cracks has a color of R.H.S. Greyed-Orange Group 177C.

The sex bud break occurs in September or October in Maryland. The sex bud break starts in the fourth or fifth year and is generally indiscernible to the untrained eye. Leaf bud break normally occurs in April in Maryland.

The specimen tree has been asexually reproduced by leaf propagation in standard growing media over the last three years. The new variety roots more readily than leaves from the other open pollinated varieties of the *Ulmus parvifolia.* The percentage of leaf rootings which take is on the order of 90 out of 100, as compared to 60–80 for tests against open pollinated leaves. The rootings made by asexual reproduction show the same vigor, growth pattern and leaf aesthetics as the originally described specimen tree.

The growth characteristics of the specimen tree are greater as compared to all the other open pollinated varieties of *Ulmus parvifolia* grown at King's Men Tree Farms.

The growth, in height, of the specimen tree is more than twice the average height of all the open pollinated trees. Only a few of the open pollinated trees reached two-thirds the height of the specimen tree.

The area of the silhouette was about two-thirds greater for the specimen tree as compared with the open pollinated trees. No open pollinated tree presented more than a 50% occulting of that caused by the specimen tree.

The above ground bulk was estimated using the cross-sectional area of the bole between the soil line and the first lateral branch measured at breast height. The bulk was found to be two and one-quarter times that of the best open pollinated trees.

I claim:

1. A new and distinct variety of elm tree as herein described and illustrated, primarily chracterized by growth rate, dendritic pattern, vigorous propagation and leaf appearance.

* * * * *